United States Patent [19]

Funk et al.

[11] Patent Number: 5,530,172

[45] Date of Patent: Jun. 25, 1996

[54] PROCESS FOR ALKANE ISOMERIZATION USING REACTIVE CHROMATOGRAPHY

[75] Inventors: Gregory A. Funk, Carol Stream; Hermant W. Dandekar, Chicago; Masami Kojima, Mount Prospect; Simon H. Hobbs, Chicago, all of Ill.

[73] Assignee: UOP, Des Plaines, Ill.

[21] Appl. No.: 333,682

[22] Filed: Nov. 3, 1994

[51] Int. Cl.[6] .................................................... C07C 5/122
[52] U.S. Cl. .................... 585/736; 585/702; 585/734; 585/738; 585/739; 585/741; 585/744; 585/746; 585/748; 585/750; 585/825
[58] Field of Search ...................... 585/702, 734, 585/736, 738, 739, 741, 744, 746, 748, 750, 825

[56] References Cited

U.S. PATENT DOCUMENTS

| | | | |
|---|---|---|---|
| 3,122,494 | 2/1964 | Brown et al. | 585/736 |
| 3,755,144 | 8/1973 | Asselin | 585/736 |
| 4,783,574 | 11/1988 | Barnes | 585/738 |
| 5,026,951 | 6/1991 | Schmidt et al. | 585/738 |
| 5,055,633 | 10/1991 | Volles | 585/825 |
| 5,146,037 | 9/1992 | Zarchy et al. | 585/738 |
| 5,233,120 | 8/1993 | Minkkinen et al. | 585/741 |
| 5,245,102 | 9/1993 | Zarchy et al. | 585/738 |

OTHER PUBLICATIONS

Badger, C. M. A.; Harris, J. A.; Scott, K. F.; Walker, M. J.; Phillips, C. S. G.; *Chromatogr.*, 1976, 126, 11–18 (No Month).

*Primary Examiner*—Asok Pal
*Assistant Examiner*—Walter D. Griffin
*Attorney, Agent, or Firm*—Thomas K. McBride; Eugene I. Snyder; Maryann Maas

[57] ABSTRACT

A process for the continuous isomerization of an alkane to produce an isomerized product through contacting the alkane with a simulated moving bed acting as a catalyst for isomerization and an adsorbent for the alkanes has been developed. The alkane may be n-butane and the isomerized product 2-methylpropane, the alkane may be n-pentane and the isomerized product 2-methylbutane or 2,2-dimethylpropane, the alkane may have from 6 up to about 8 carbon atoms with no more than one methyl branch and the isomerized product having the same number of carbon atoms and at least two methyl branches, or the reactant may be a mixture of the foregoing alkanes with the corresponding isomerized products being formed. In a zone of the simulated moving bed, the alkanes are catalytically isomerized to form the isomerized products. The unreacted alkanes are adsorbed, and the isomerized products are collected. In a subsequent zone of the simulated moving bed, the unreacted alkanes are desorbed using a desorbent and are catalytically isomerized to form additional isomerized products which are also separated and collected.

13 Claims, 1 Drawing Sheet

PROCESS FOR ALKANE ISOMERIZATION USING REACTIVE CHROMATOGRAPHY

BACKGROUND OF THE INVENTION

Alkane isomerization processes are widely used by refiners to convert normal $C_4$ and $C_5$ alkanes and normal and mono-methyl-branched $C_6$ alkanes into more valuable branched alkanes. The multi-methyl-branched $C_6$ alkanes have a higher octane number and are used as gasoline blending components to boost the octane number of the gasoline. The mono-methyl-branched $C_4$ and $C_5$ alkanes may also be used as intermediates, after dehydrogenation, for such oxygenate products as methyl tertiary butyl ether, ethyl tertiary butyl ether, and tertiary amyl methyl ether.

Typically, commercial isomerization processes have had at least a two-stage design; the first stage is a fixed bed reactor, and the second stage is a separation unit. See, for example, U.S. Pat. Nos. 5,146,037 and 5,245,102. The isomerization that takes place in the fixed bed reactor is limited by thermodynamic equilibrium, which results in the reactor effluent containing a substantial amount of unconverted alkanes. The separation unit, which is usually either an adsorption or a fractionation unit, is used to separate the unconverted alkanes from the isomerized product alkanes. The unconverted alkanes are generally recycled to the fixed bed reactor. With this type of design, the recycle stream is usually substantial, and methods of increasing the yield of highly branched alkanes are in demand.

Normal and mono-methyl-branched alkanes containing 7 or more carbon atoms have been converted into benzene and other valuable aromatic hydrocarbons for gasoline blending by catalytic reforming. However, due to environmental concerns, the demand for aromatics in the future may diminish. An alternate refining process for the normal and mono-methyl-branched $C_7$ and $C_8$ alkanes that yields a high octane number product is the present invention of alkane isomerization by reactive chromatography. Prior to the current invention, $C_7$ and $C_8$ alkanes were not isomerized due to the extensive cracking of the desired highly branched alkane products. However, with the rapid removal of the highly branched products in the current invention, the amount of cracking is reduced and the product dimethyl- and trimethyl- $C_7$ and $C_8$ alkanes are formed. The isomerized $C_7$ and $C_8$ products may be used as octane number boosters in gasoline blending instead of benzene and other aromatics.

The present invention makes use of both simulated moving bed technology and reactive chromatography to perform isomerization of hydrocarbons containing from about 4 to about 8 carbon atoms. Reactive chromatography allows for concurrent isomerization and separation of the unconsumed reactants from the products, thereby extending product yields beyond thermodynamic equilibrium limitations. Others have attempted concurrent alkane isomerization and separation, but only using fixed bed systems. For example, Badger, C. M. A.; Harris, J. A.; Scott, K. F.; Walker, M. J.; Phillips, C. S. G. *J. Chromatogr.* 1976, 126, 11–18, disclosed placing a catalyst in a gas chromatography column and having a heater move along the length of the column to catalyze isomerization and effect separation.

Also, U.S. Pat. No. 4,783,574 disclosed a fixed bed reactor containing two sub-beds of adsorbent at opposite ends of the reactor and one sub-bed of catalyst in the center of the reactor. The feed was introduced near the catalyst sub-bed, and a desorbent was introduced at one end of the reactor. The isomerization was catalyzed and unconsumed reactants were adsorbed on the adsorbent sub-bed downstream of the catalyst sub-bed in the direction of the desorbent flow. Then the desorbent flow was reversed by introducing the desorbent from the opposite end of the reactor to desorb the unconsumed reactants and carry them back to the catalyst sub-bed. The present invention is significantly distinct from the art. The present invention is operated in a simulated moving bed mode, and incorporates a homogeneous mixture of catalyst and adsorbent in every sub-bed.

SUMMARY OF THE INVENTION

The purpose of this invention is to provide a process for the continuous isomerization of an alkane to produce an isomerized product through contacting the alkane with a simulated moving bed acting as a catalyst for isomerization and an adsorbent for the alkanes. The alkane may be n-butane and the isomerized product 2-methylpropane, the alkane may be n-pentane and the isomerized product 2-methylbutane or 2,2-dimethylpropane, the alkane may have from 6 up to about 8 carbon atoms with no more than one methyl branch and the isomerized product having the same number of carbon atoms and at least two methyl branches, or the reactant may be a mixture of the foregoing alkanes with the corresponding isomerized products being formed. In a zone of the simulated moving bed, the alkanes are catalytically isomerized to form the isomerized products. The unreacted alkanes are adsorbed, and the isomerized products are collected. In a subsequent zone of the simulated moving bed, the unreacted alkanes are desorbed using a desorbent and are catalytically isomerized to form additional isomerized products which are also separated and collected.

BRIEF DESCRIPTION OF THE DRAWING

The figures depicts two schematic representations of a simulated moving catalyst and adsorbent bed process at two different points in time, modified and operated in accordance with the process of this invention. The drawings have been simplified by the deletion of a large number of pieces of apparatus customarily employed on a process of this nature which are not specifically required to illustrate the performance of the subject invention.

DETAILED DESCRIPTION OF THE INVENTION

Figure 1A:
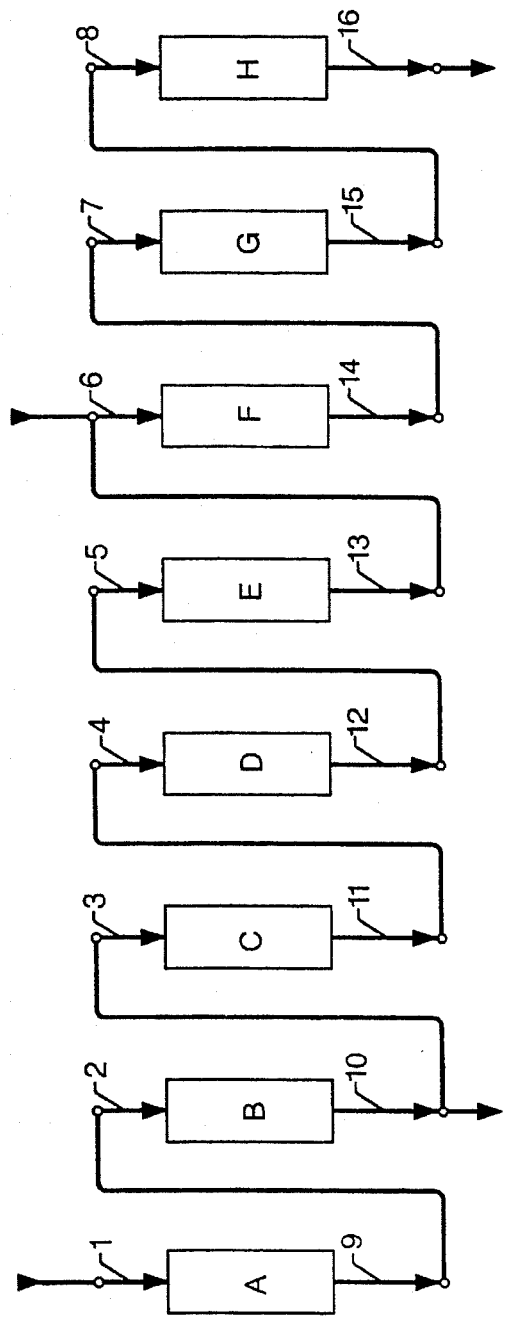

The invention is a process for the continuous isomerization of alkanes to form isomerized products using a simulated moving bed to effect reactive chromatography, i.e., a process where a simulated moving bed both catalyzes the isomerization reaction and effects the separation of the alkane reactants from the isomerized products. In general terms, the alkane reactants are contacted with a simulated moving bed of a mixture of solids. The bed is effective to both catalyze isomerization and to separate the isomerized products from the alkane reactants through adsorption of at least the reactants. The now separated isomerized products are continuously removed from the simulated moving bed and collected. The adsorbed alkane reactants are desorbed by a desorbent and, since they are still in contact with the simulated moving bed, they are catalytically isomerized to form additional isomerized products which are also separated and collected. The process continues in this fashion, with alkane reactants being retained by the adsorbing properties of the simulated moving bed until they are isomerized to form the desired isomerized products which are then separated and collected. The alkane reactant may be: n-butane with the isomerized product being 2-methylpropane; n-pentane with the isomerized product being 2-methylbutane or 2,2-dimethylpropane; an alkane having from 6 up to about 8 carbon atoms with no more than one methyl branch and the isomerized product having the same number of carbon atoms and at least two methyl branches; or the reactant may be a mixture of the foregoing alkanes with the corresponding isomerized products being formed.

Both reactive chromatography and simulated moving bed technology are known in the art, and a general discussion of these technologies may be found in Mowry, J. R. In *Handbook of Petroleum Refining Processes*; Meyers, R. A. Ed.; McGraw-Hill New York, 1986; pp 8–79 to 8–99 for the simulated moving bed technique; and *Preparative and Production Scale Chromatography*, Ganetsos, G., Barker, P. E., Eds.; Chromatographic Science Series Vol. 61; Marcel Dekker: New York, 1993; Chapters 16–21 for reactive chromatography. Applicants have realized that these technologies may be effectively applied to the isomerization of alkanes to form isomerized products, and the details of reactive chromatography and simulated moving bed technique as applied to the instant invention are supplied below.

Reactive chromatography requires that the desired reaction and the separation of the products and reactants occur concurrently. Therefore, the simulated moving bed of the present invention must perform dual functions. The mixture of solids forming the simulated moving bed must be effective as a catalyst for the isomerization reaction and also must be effective as an adsorbent which preferentially retains at least the alkane reactants in order to separate them from the isomerized products. When the alkane reactants enter the bed and contact the mixture of solids, the isomerization reaction is catalyzed and isomerized products are formed. The isomerization reaction primarily takes place in the portion of the solid bed adjacent to and immediately downstream in the direction of the fluid flow of the introduction point of the feed, which contains at least one of the alkane reactants. Not all the alkane reactants will immediately react. Since the mixture of solids is also effective as an adsorbent for the alkane reactants, the isomerized products and the alkane reactants begin to undergo separation. The isomerized products which are less strongly adsorbed by the adsorbent are carried with the fluid flow, and the alkane reactants which are strongly adsorbed by the adsorbent are carried countercurrently with the simulated movement of the solids. The migration of the alkane reactants and isomerized products in opposite directions results in one region of the bed being richer in isomerized products and one region of the bed being richer in alkane reactants. Once separated, the isomerized products carried by the fluid flow are removed from the product rich region of the bed in a raffinate stream and collected. Concurrently, the alkane reactants carried by the adsorbent are desorbed at the reactant rich region of the bed by the introduction of a desorbent. The desorbed alkane reactants, still being in contact with the simulated moving bed, are catalytically isomerized and form additional isomerized products which are then carried with the fluid flow and collected. The process operates continuously with the alkane reactants being introduced, the isomerization being catalyzed, and the isomerized products being separated from the alkane reactants and collected, the alkane reactants being isomerized to form additional isomerized products which are also separated and collected. Due to the continuous separation and removal of the isomerized products, the thermodynamic equilibrium constraint of a static system is no longer a limiting factor and the isomerization continues, resulting in a much greater conversion to isomerized products. As a result, the external recycle of unconsumed reactants is greatly reduced or eliminated, thereby affording a substantial savings in operating costs.

As previously discussed, the simulated moving bed is made up of a mixture of solids which together are effective to both catalyze the isomerization reaction and to separate the isomerized products from the alkane reactants. Two or more solids, at least one being an isomerization catalyst and at least one being an adsorbent, are used as a homogeneous mixture. Different isomerizations and separations may require different catalyst and adsorbent combinations or different volume ratios of catalyst to adsorbent. Typically, catalyst to adsorbent volume ratios range from about 1:19 to about 19:1 with a preferred range of from about 1:9 to about 9:1.

A wide variety of solid catalysts and adsorbents are available, and each isomerization application may require a different combination of solids. The solid or solids acting as a catalyst may be any of the commonly used isomerization catalysts including, but not limited to, platinum on mordenite, aluminum chloride on alumina, and platinum on sulfated metal oxides such as zirconia. See generally, Kirk-Othmer *Encyclopedia of Chemical Technology*, 3rd ed.; Grayson, M., Eckroth, D., Eds.; John Wiley & Sons: New York, Vol. 11 p. 664, Vol. 12 pp. 911 and 922, and Vol. 15 p. 651. Depending upon the composition of the feed, several different catalysts may be combined in order to accomplish the catalysis function. The preferred catalysts are platinum on mordenite or on sulfated zirconia.

The adsorbent solid or solids are selected to either have a pore size capable of admitting alkane reactants but not the isomerized products, or an affinity for alkanes with no or low branching. Examples of suitable adsorbents include, but are not limited to, silicalite, ferrierite, Ca-A zeolite, MAPO-31, SAPO-31, SAPO-11 and combinations thereof. Depending upon the composition of the feed, several different adsorbents may be combined in order to accomplish the separation function. For example when the feed contains $C_6$ to $C_8$ alkanes, a portion of the adsorbent should retain both normal and mono-methyl-branched alkanes, so that they are retained in the bed until they are isomerized to form multi-methyl-branched isomerized products. A preferred adsorbent capable of retaining both normal and mono-methyl-branched alkanes is silicalite. When the feed contains n-butane or n-pentane, a portion of the adsorbent should retain only normal alkanes, since the $C_4$ and $C_5$ mono-methyl-branched alkanes re isomerized products which are collected. A preferred adsorbent capable of retaining only normal alkanes is Ca-A zeolite. The adsorbents may be combined in different volume ratios depending upon the composition of the feed. As an illustration, in an embodiment where the adsorbent is a mixture of Ca-zeolite and another adsorbent and the feed contains n-butane or n-pentane, the greater the concentration of n-butane or n-pentane present in the feed increases, the greater the required concentration of Ca-A zeolite in the adsorbent mixture, or in an embodiment where the adsorbent is a mixture of silicalite and another adsorbent and the feed contains $C_6$ to $C_8$ alkanes, the greater the concentration of $C_6$ to $C_8$ alkanes present in the feed, the greater required the concentration of silicalite in the adsorbent mixture.

The catalyst and adsorbent mixture of solids, once chosen, is used in the process in the form of a simulated moving bed where the bed is held stationary, and the locations at which the various streams enter and leave the bed are periodically moved. The bed itself is usually a succession of fixed sub-beds, and different isomerization reactions may require differing numbers of sub-beds. The most commonly used range is from about 4 sub-beds to about 24 sub-beds with the preferred range being from about 6 to about 24 sub-beds, and the most preferred range being from about 6 to about 8 sub-beds. The sub-beds are housed in individual interconnected chambers, and each chamber is equipped with an inlet and an outlet line.

The shift in the locations of input and output streams in the direction of the fluid flow through the bed simulates the movement of the solid bed in the opposite direction. Commercially, moving the locations of the input and output streams may be accomplished by a variety of fluid directing devices such as rotary valves or a network of two-position or multi-position valves which work in conjunction with the inlet and outlet lines of the sub-beds. The fluid directing device accomplishes moving the locations of the input and output streams through first directing the streams to the appropriate inlet or outlet lines of the sub-beds. After a specified time period called the step time, the fluid directing device advances one index and redirects the streams to the inlet or outlet line immediately adjacent and downstream of the previously used inlet or outlet line. Each advancement of the fluid directing device to a new position is generally called a step, and the completion of all the valve steps is called a cycle. The step time is uniform for each step in a cycle, and the cycle time ranges generally from about 5 minutes to about 3 hours.

The principal inputs and outputs of the simulated moving bed system consist of four streams: the desorbent, the feed, the extract, and the raffinate. Each stream flows into or out of the simulated moving bed at individual locations and at a particular flow rate which is independently controlled.

The desorbent, which is introduced to the simulated moving bed system, may be a nonreactive material capable of displacing the selectively adsorbed alkane reactants from the bed, or the desorbent may be one of the alkane reactants which is also capable of displacing the other selectively adsorbed alkane reactants from the bed. Suitable desorbents include but are not limited to hydrogen, nitrogen, methane, ethane, propane, butane, pentane, and mixtures thereof. The preferred desorbent for feeds containing $C_6$ to $C_8$ alkanes is n-pentane. When the feed contains only $C_4$ and $C_5$ alkanes suitable desorbents include hydrogen, nitrogen, methane, ethane, and propane. The flow rate of the desorbent stream is typically from about 0.5 to about 35 times that of the feed rate (discussed below). When the desorbent is a compound which is also a reactant, the compound may or may not be included and additionally introduced in the alkane reactant mixture. An example of this variant is using normal pentane both as the desorbent and as a reactant to form 2-methylbutane and 2,2-dimethylpropane.

Using a desorbent which is also a reactant brings added benefits which are not readily apparent and which derive from the isomerization of the desorbent incident to its use as a desorbent. In particular, the branched alkanes which result from the isomerization are themselves octane boosters which may be blended into gasoline, thereby achieving an incremental octane increase beyond that achieved when the desorbent is not a reactant.

Another quite unexpected benefit arises from the differential desorption capability of the branched alkanes relative to the normal alkanes. Isomerization of the normal alkane desorbent is predominately accomplished in the portion of the simulated moving bed adjacent to and downstream in the direction of the fluid flow of the desorbent input. Since the branched alkanes are less strongly adsorbed by the adsorbent than are the normal alkanes, there is a consequence of greater adsorption capability for reactants resulting in greater efficiency of the separation.

The feed introduced to the simulated moving bed system contains at least one alkane which is to undergo catalytic isomerization to form at least one isomerized product. Examples of suitable alkanes include, normal butane, normal pentane, 2-methylbutane, normal hexane, 2-methylpentane, 3-methylpentane, normal heptane, 2-methylhexane, 3-methylhexane, normal octane, 2-methylheptane, 3-methylheptane, and 4-methylheptane. Preferably the feed contains normal hexane, 2-methylpentane, 3-methylpentane, n-heptane, 2-methylheptane, 3-methylheptane, and 4-methylheptane. The feed is usually derived from other refinery processes and may contain cyclic alkanes, olefinic hydrocarbons, aromatic hydrocarbons, and other hydrocarbons. The feed may also be the effluent of a fixed bed isomerization unit where alkane reactants and the corresponding isomerized products are present in amounts determined by the conversion in the fixed bed which is limited by thermodynamic equilibrium. The liquid hourly space velocity of the feed stream is typically from about 0.05 to about 5.

The extract and the raffinate are both withdrawn from the simulated moving bed system. The raffinate contains desorbent and the isomerized products which were less strongly adsorbed by the adsorbent and were carried with the fluid flow. Examples of the isomerized products found in the raffinate include, 2-methylpropane, 2-methylbutane, 2,2-dimethylpropane, 2,3-dimethylbutane, 2,2-dimethylbutane, 2,2-dimethylpentane, 3,3-dimethylpentane, 2,3-dimethylpentane, 2,4-dimethylpentane, 2,2,3-trimethylbutane, 2,2-dimethylhexane, 3,3-dimethylhexane, 2,3-dimethylhexane, 3,4-dimethylhexane, 2,4-dimethylhexane, 2,5-dimethylhexane, 2,2,3-trimethylpentane, 2,3,3-trimethylpentane, 2,3,4-trimethylpentane, and 2,2,4-trimethylpentane. Downstream fractionation may be used to separate desorbent from the isomerized products. The desorbent may be recycled, and the isomerized products collected.

The extract contains desorbent and the separated materials which were selectively adsorbed by the adsorbent and then desorbed by the desorbent. The purpose of the extract stream is to prevent the buildup of impurities. Therefore, the desired components in the extract stream include the cyclic alkanes, aromatic hydrocarbons, and other undesired hydrocarbons that were present in the feed or that were produced as undesired by-products of the process. Since the alkane reactants will be desorbed along with the impurities, it is expected that the extract stream will also remove some alkane reactants, desorbent, and perhaps some isomerized products. To minimize this undesired loss, the flow rate of the extract stream is greatly reduced as compared to the flow rate of other streams, and the amount of extract removed depends on the amount of impurities present and undesired by-products being generated. The alkane reactants, desorbent, and isomerized products removed in the extract stream may be recovered by distillation, the isomerized products collected, the alkane reactants recycled to the feed, and the desorbent recycled to the simulated moving bed.

As an option, a second desorbent stream may be introduced to the simulated moving bed between the feed input and the raffinate output. This desorbent stream would function to reduce the residence time of isomerized products and thereby minimize cracking of the higher carbon number products. Suitable desorbents for this variant include those already discussed above.

Typically in a commercial system, the four principal streams are spaced strategically throughout the simulated moving bed system and divide the sub-beds into three zones, each of which performs a different function. Zone I contains the sub-beds located between the feed input and the raffinate output. The majority of the isomerization reaction and the adsorption of at least the alkane reactants takes place in this zone. Zone II contains the sub-beds located between the extract output and the feed input. In this zone, there is some further reaction as the more selectively adsorbed alkane reactants are desorbed and come into contact with the catalyst. Zone III contains the sub-beds located between the desorbent input and the extract output. The main purpose of this zone is to completely desorb all alkane reactants and any impurities or reaction by-products from the adsorbent.

Operating conditions will depend upon the catalyst and adsorbent selected. Typical operating temperatures for the process are about 100° C. to about 500° C., preferably from about 150° to about 250° C. Typical operating pressures for the process are about $2.5 \times 10^5$ to about $1.72 \times 10^6$ N/m², preferably from about $7.5 \times 10^5$ to about $1.72 \times 10^6$ N/m². As outlined above, the process conditions are set so that all the streams are in the gas phase.

Without intending any limitation on the scope of the present invention and as merely illustrative, this invention is explained below in specific terms as applied to one specific embodiment of the invention, the continuous isomerization of n-hexane, 2-methylpentane, and 3-methylpentane to form 2,2-dimethylbutane and 2,3-dimethyl butane using a mixture of silicalite and platinum on mordenite in a 3:1 volume ratio to effect catalysis of the isomerization and the separation of the products and reactants through adsorption. For ease of understanding, the process of the invention described below is limited to having eight sub-beds. The necessary apparatus is first described and then the process of the invention as applied to the embodiment is discussed.

Figure 1B:
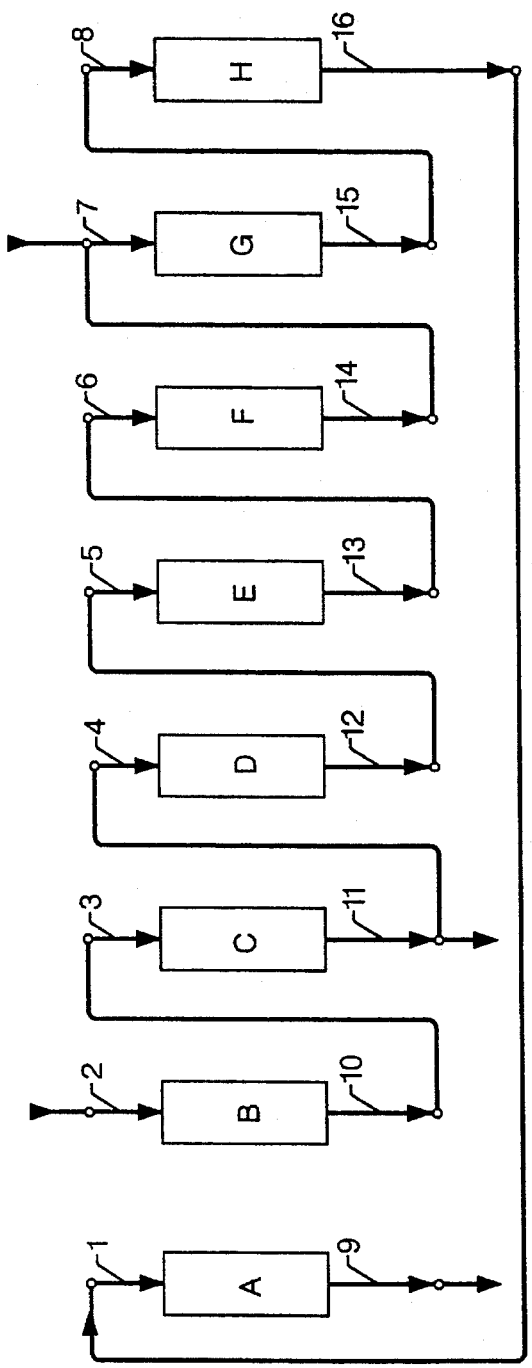

Referring now to FIGS. 1A and 1B, the simulated moving bed is made up of eight sub-beds, labeled A–H. Each sub-bed is provided with an inlet line, indicated as 1–8, and an outlet line, indicated as 9–16. Each inlet line may be used to introduce the desorbent, introduce the feed, or introduce the effluent from the previous sub-bed. Each outlet line may be used to withdraw the extract, withdraw the raffinate, or direct the effluent to the next sub-bed. Each of the inlet and outlet lines are connected to fluid directing and flow control apparatus (not shown). The fluid directing apparatus allows the principal streams, the feed, the desorbent, the extract and the raffinate, to be sequentially directed to the next successive sub-bed in the direction of the fluid flow. The continued progression of the streams will simulate the movement of the solid bed in the countercurrent direction. The fluid directing apparatus also controls the interconnection of the sub-beds.

The upper diagram, labeled FIG. 1A, shows the inlet and outlet lines at the starting position. The desorbent is introduced to the simulated moving bed through inlet line 1, and the feed is introduced to the simulated moving bed through inlet line 6. The extract is withdrawn from the simulated moving bed through outlet line 10 and the raffinate is withdrawn from the simulated moving bed through outlet line 16. The effluent of sub-beds A through G are conducted through the outlet line of each sub-bed, lines 9–15 respectively, and connected to the inlet line of the next successive sub-bed, lines 2–8 respectively, in order to conduct the effluent from sub-bed to sub-bed. The effluent of the sub-bed from which the raffinate is withdrawn, H, is not routed to the next successive sub-bed since the entire effluent is collected as the raffinate. Breaking the interconnections at this point also prevents backflow of the desorbent being introduced at the inlet of the next successive sub-bed, A.

To demonstrate the progression of the simulated moving bed, the lower diagram, labeled FIG. 1B, shows the configuration of the lines after the fluid directing apparatus has advanced one step. Now the desorbent is introduced to the simulated moving bed through inlet line 2, and the feed is introduced to the simulated moving bed through inlet line 7. The extract is withdrawn from the simulated moving bed through outlet line 11 and the raffinate is withdrawn from the simulated moving bed through outlet line 9. The effluent of sub-beds B through H are conducted through the outlet line of each sub-bed, lines 10–16 respectively, and connected to the inlet line of the next successive sub-bed, lines 3–8 and line 1 respectively, in order to conduct the effluent from sub-bed to sub-bed. The effluent of the sub-bed from which the raffinate is withdrawn, A, is not routed to the next successive sub-bed since the entire effluent is collected as the raffinate. Each successive step of the fluid directing apparatus would advance the location of the streams in a similar manner.

Using the described apparatus, the invention is performed as follows. The flow rates of each of the principal streams and the step time of fluid directing apparatus may be first set to selected values based on the operator's experience. Note that the rate of the extract stream will be set to a greatly reduced flow rate as compared to the other streams. Due to the cyclic nature of the process, the starting position of the location of the streams is not important; for this illustration the starting position of the streams are as depicted in the diagram labeled FIG. 1A. When the feed containing the alkane reactants, n-hexane, 2-methylpentane, and 3-methylpentane, conducted in inlet line 6, enters the simulated moving bed sub-bed F and contacts the homogeneous mixture of silicalite and platinum on mordenite, the isomerization reaction is catalyzed, and highly branched paraffins, 2,2-dimethylbutane and 2,3-dimethylbutane, are formed. The 2,2-dimethylbutane and 2,3-dimethylbutane products, which are only weakly absorbed by the silicalite, are carried with the fluid flow and withdrawn from the bed in the raffinate stream conducted from sub-bed H in outlet line 16. The n-hexane, 2-methylpentane, and 3-methylpentane reactants and any impurities, which are absorbed by the silicalite, are carried with the solid bed in its countercurrent simulated movement thereby being separated from the 2,2-dimethylbutane and 2,3-dimethylbutane products. The n-hexane, 2-methylpentane, and 3-methylpentane reactants and any impurities are desorbed from the silicalite adsorbent by the propane desorbent which is conducted to sub-bed A through inlet line 1. Note, the propane desorbent will most likely contain some hydrogen for catalyst stability. The n-hexane, 2-methylpentane, and 3-methylpentane reactants, once desorbed, again contact the platinum on mordenite catalyst and are isomerized to form additional 2,2-dimethylbutane and 2,3-dimethylbutane products. The newly formed 2,2-dimethylbutane and 2,3-dimethylbutane products are carried with the fluid flow and removed in the raffinate stream. The impurities and some alkane reactants and isomerized products are withdrawn from the sub-bed B in the extract stream conducted through outlet line 10.

It must be emphasized that the above description is merely illustrative of an embodiment and is not intended as an undue limitation on the generally broad scope of the invention. Moreover, while the description is narrow in scope, one skilled in the art will understand how to extrapolate to the broader scope of the invention. For example, operation of the invention where a second desorbent stream is introduced to a sub-bed between where the feed is introduced and where the raffinate is withdrawn can be readily extrapolated from the foregoing description. Similarly, one skilled in the art would understand how the above process is applied where the desorbent is normal pentane, or where the feed stream contains a different composition such as normal butane and normal pentane. Furthermore, the optimum number of sub-beds, the optimum cycle time, and the optimum flow rates for a given application would be readily determined by one skilled in the art.

What is claimed is:

1. A process for the gas phase isomerization of an alkane to an isomerized product having the same carbon number, wherein
   i) said alkane is n-butane and the isomerized product is 2-methylpropane, or
   ii) said alkane is n-pentane and the isomerized product is 2-methylbutane or 2,2-dimethylpropane, or
   iii) said alkane has from 6 up to about 8 carbon atoms with no more than one methyl branch and the isomerized product has at least two methyl branches, said process comprising:
   a. continuously introducing, under conditions effective to isomerize the alkane to the isomerized product, the alkane and a desorbent into a simulated moving bed of a mixture of solids wherein the mixture of solids contains a catalyst effective to isomerize the alkane and an adsorbent effective to selectively adsorb the alkane relative to the isomerized product;
   b. isomerizing at least a portion of the alkane to at least one isomerized product in a zone of the simulated moving bed with concurrent separation of the isomerized products formed using the adsorbent;
   c. desorbing the alkane from the adsorbent using the desorbent in a subsequent zone of the simulated moving bed and continuing the isomerization of the alkane with concurrent separation of the isomerized product(s) formed thereby using the adsorbent; and
   d. removing and collecting the isomerized products from the simulated moving bed.

2. The process of claim 1 wherein the catalyst is selected from the group consisting of platinum on mordenite, aluminum chloride on alumina, and platinum on sulfated metal oxides, and the adsorbent is selected from the group consisting of silicalite, ferrierite, Ca-A zeolite, MAPO-31, SAPO-31 and SAPO-11.

3. The process of claim 1 wherein the catalyst and adsorbent are present in a volume ratio of about 1:19 to about 19:1.

4. The process of claim 1 wherein the catalyst and adsorbent are present in a volume ratio of about 1:9 to about 9:1.

5. The process of claim 1 wherein the desorbent is selected from the group consisting of hydrogen, nitrogen, methane, ethane, propane, butane, and pentane.

6. The process of claim 1 further comprising wherein the desorbent is a normal alkane capable of undergoing isomerization to form a branched alkane, and at least a portion of the desorbent is isomerized to form the branched alkane.

7. The process of claim 1 further comprising wherein the desorbent is normal pentane and at least a portion of the normal pentane is isomerized to form branched pentanes.

8. The process of claim 1 further comprising a second desorbent continuously introduced to the simulated moving bed.

9. The process of claim 8 wherein the second desorbent is selected from the group consisting of hydrogen, nitrogen, methane, ethane, propane, butane, and pentane.

10. The process of claim 1 wherein the catalyst is platinum on mordenite and the adsorbent is silicalite.

11. The process of claim 1 wherein the alkane is n-butane, n-pentane, or a combination thereof, and the adsorbent is Ca-A zeolite.

12. The process of claim 1 wherein the alkane has from 6 up to about 8 carbon numbers with no more than one methyl branch, and the adsorbent is silicalite.

13. The process of claim 1 wherein the simulated moving bed further comprises a feed stream, a desorbent stream, a raffinate stream, and an extract stream, each with individual flow control.

* * * * *